United States Patent [19]

Chowhan

[11] Patent Number: 4,490,377

[45] Date of Patent: Dec. 25, 1984

[54] ACID STABILIZED COMPOSITIONS OF THIENO-PYRIDINE DERIVED COMPOUNDS

[75] Inventor: Zaka-Ud-Din T. Chowhan, Sunnyvale, Calif.

[73] Assignee: Syntex (U.S.A.) Inc., Palo Alto, Calif.

[21] Appl. No.: 376,878

[22] Filed: May 10, 1982

Related U.S. Application Data

[63] Continuation-in-part of Ser. No. 173,310, Jul. 29, 1980, abandoned.

[51] Int. Cl.$^3$ .................... C07D 513/04; A61K 31/44
[52] U.S. Cl. ..................................... 424/256; 546/114
[58] Field of Search ......................... 546/114; 424/256

[56] References Cited

U.S. PATENT DOCUMENTS 3,903,095  9/1975  Shen et al. .......................... 546/114
4,051,141  9/1977  Castaigne ........................... 546/114

OTHER PUBLICATIONS

The Merck Index, Ninth Edition, pp. 300 and 583, Pub. by Merck & Co., Inc., (1976).
Remington's Pharmaceutical Sciences, Fourteenth Edition, Mack Pub. Co., pp. 302, 303, 1316, 1317, 1474 and 1475, (1970).
The Merck Index, Ninth Edition, pp. 110–111, (1976).

*Primary Examiner*—Alan L. Rotman
*Attorney, Agent, or Firm*—James M. Kanagy; Tom M. Moran

[57] ABSTRACT

A stable pharmaceutical composition which comprises an acid salt of a thieno-pyridine derived compound, a pharmaceutically acceptable, non-volatile acid and optionally other suitable pharmaceutical excipients.

10 Claims, No Drawings

ACID STABILIZED COMPOSITIONS OF THIENO-PYRIDINE DERIVED COMPOUNDS

This application is a continuation-in-part of application Ser. No. 173,310 filed July 29, 1980 now abandoned.

BACKGROUND OF THE INVENTION

1. Field of the Invention

This invention relates to the stabilization of a pharmaceutical composition containing acid salts of thieno-pyridine derivatives. The stabilization is achieved using a pharmaceutically acceptable, non-volatile acid, particularly citric acid.

2. Prior Art

Because of the need to facilitate manufacture, application or consumption of the drug, control of the unit dose, and ease of packaging and handling, drugs are commonly manufactured and marketed in combination with other ingredients of little or no therapeutic value. Against these considerations must be reflected the need to maintain the stability of the composition over the shelf life of the formulation in order to maintain the unit dose and to avoid any untoward effects which may arise from degradation of the drug or excipients.

Initially prepared pills and capsules of compositions containing a thieno-pyridine derived drug named ticlopidine hydrochloride (see U.S. Pat. No. 4,051,141) discolored during normal storage. Analysis of these materials showed degradation of ticlopidine was responsible for the discoloration. The presence of certain excipients such as gelatin, Povidone and magnesium stearate was determined to be the initiating factor in this degradation. In order to market an efficacious and acceptable drug of this structure in the proposed formulation, a means was needed for preventing this degradation which would not interfere with the action of the drug nor have a detrimental or deleterious effect on the user.

No information in the literature deals directly with the prevention of degradation in compositions of thieno-pyridine compounds insofar as is known.

One class of anti-oxidant and chelating agent additives for stabilizing organic compounds and compositions is non-volatile organic acids. For example ascorbic acid and citric acid as well as malic acid and tartaric acid have all been used as stabilizers. Citric acid in particular has been used to stabilize fats and oils (U.S. Pat. Nos. 2,197,269 and 3,294,825), hydroquinone solutions (U.S. Pat. No. 3,855,150), and drugs such as fluocinolone acetonide (Great Britain Pat. No. 41034/62), PGE series compounds (German Pat. No. 2,353,797) and L-Dopa formulations (J7 9014-167). None of these references suggest, however, that citric acid or others of that additive class would be useful in stabilizing acid addition salts of thieno-pyridine compounds in solid dosage formulations, such as capsules and tablets.

SUMMARY OF THE INVENTION

It has been discovered that addition of a non-toxic amount of a non-volatile acidic compound having a pKa between 2-6 to acid addition salts of thieno-pyridine derived compounds in dry formulations effectively prevented discoloration under normal manufacturing and storage conditions and does not interfere with other considerations of drug efficacy.

Thus one aspect of this invention is a composition which comprises a non-toxic stabilizing amount of a pharmaceutically acceptable non-volatile acidic compound and a therapeutically effective amount of an active ingredient which is a pharmaceutically acceptable acid addition salt of a thieno-pyridine derived compound chosen from those represented by the formula

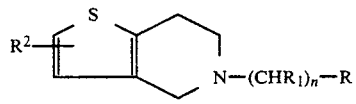

Formula I wherein:

R is phenyl or benzyl, each optionally substituted on the phenyl ring with 1 to 3 halogen atoms, alkyl of 1–6 carbon atoms, alkoxy of 1–6 carbon atoms, hydroxy or nitro;

$R_1$ is hydrogen, halogen, hydroxy or alkyl having 1–6 carbon atoms;

$R_2$ is hydrogen or halogen; and n is 1 or 2, and when n is 2, $R_1$ may have different meanings in each ($CHR_1$) radical. Of particular interest is the compound 5-(2-chlorobenzyl)-4,5,6,7-tetrahydro-thieno[3,2,c]-pyridine HCl (ticlopidine-HCl).

Other pharmaceutically acceptable excipients may be present such as a lubricant, a disintegrant, an extender and a binder.

Another aspect of this invention is a process for preventing degradation of an acid addition salt of formula I type compounds, which process comprises adding a non-toxic stabilizing amount of a pharmaceutically acceptable non-volatile acidic compound to a dry powder formulation containing one or more of said compounds and excipients, for example, a binder, a lubricant, a disintegrant and an extender.

FURTHER DESCRIPTION OF THE INVENTION

The method of practicing this invention may be carried out by developing a formulation for acid addition salts of thieno-pyridine derived compounds, for example, those of formula I, above, which includes the drug in a pharmaceutically therapeutic amount, a non-toxic stabilizing amount of a pharmaceutically acceptable non-volatile acidic compound, a lubricant, a binder, a disintegrant, and a diluent. Both tablets and capsules may be prepared from this formulation.

This invention is applicable to any acid salt of a thieno-pyridine derived compound of formula I, above, with, for example, inorganic acids such as hydrochloric acid, hydrobromic acid, sulfuric acid, nitric acid or phosphoric acid; or organic acids such as acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid and the like. The hydrochloric acid (HCl) salt is preferred. Generally, a therapeutically effective amount of the acid salt will be that amount necessary to give the desired pharmacological effect, and will constitute about 40–90% by weight per unit formulation. A unit formulation is a pill or capsule containing a therapeutic amount of said drug plus any added excipients.

A pharmaceutically acceptable non-volatile acidic compound is one which is crystalline at room temperature and remains so throughout the range of temperatures normally encountered in the manufacture and storage of pharmaceutical compositions and has a pKa between 2-6. Such a compound may be an inorganic or organic acid or acidic salt thereof. Organic acids whose primary utility is therapeutic are not suggested for use herein, not because they would not stabilize the instant compositions but because their presence in conjunction with thieno-pyridine compounds may not be medically indicated or desired. Acetylsalicylic acid is specifically excluded from this invention.

A non-toxic, stabilizing amount of acid is that amount which will prevent active ingredient degradation but will not exhibit unacceptable localized or systemic toxic effects on the consumer. Composition stabilization is dependent on a variety of factors such as the acidic compound employed, the type of excipients used, excipient amounts, formulation processes, and in part the amount of active ingredient and its acid salt. Because of these several factors, empirical methods are best used for determining exactly how much acidic compound will stabilize a given thieno-pyridine acid addition salt formulation. What constitutes a stabilizing amount can readily be determined by experimental procedures which are well within the skill of one of ordinary skill in the formulation arts. For example, preparation of several compositions containing active ingredient and increasing amounts of acidic compound, and then observing these formulations for color changes, will quickly reveal which concentrations of a particular acidic compound adequately inhibits decomposition. Such experiments are well within the skill of the routineer in the art and do not require undue experimentation.

A preferred practice of this invention involves using about 0.5–5.0% (w/w) of a stabilizing acidic compound relative to the total amount of active ingredient. It has been found that this amount of acidic compound is adequate to prevent tablet and powder discoloration while not interfering with other formulation and therapeutic considerations. However, there may be circumstances and conditions under which a larger percentage of stabilizing acidic compound effectively could be used. Such situations are within the scope of this invention. A more preferred range for stabilizing acidic compound concentrations is 0.5–3% (w/w) with 1.0–1.5% (w/w) being most preferred.

The amount of acidic compound employed herein to stabilize these compositions also should take into account toxicity considerations. In any practice of this invention only a non-toxic amount of acidic compound will be used to stabilize the active ingredient. The amount of acidic compound used herein should not be so large as to cause unacceptable and unwarranted localized or systemic toxicity. All acidic compounds falling within the recited definition herein are not toxic within the preferred ranges set out above.

Inorganic acidic compounds are represented by monobasic alkali metal phosphates pyrophosphates, metaphosphates orthophosphate and the like; monobasic alkali metal salts of sulfuric acid and nitric acid or similiar salts which have one or more protons and the requisite pKa. Representative of organic compounds are ascorbic acid, malic acid, tartaric acid, glycolic acid, malonic acid, malic acid, maleic acid, fumaric acid, benzoic acid, cinnamic acid, mandelic acid, and the like. Of these, citric acid is preferred.

A lubricant is generally some fatty acid derived compound or mineral oil which is blended with the formulation to lubricate the punches and die used to form pills and fill capsules. Any lubricant known to the art may be used to practice this invention, for example, magnesium stearate, calcium stearate, stearic acid, lubriwax, mineral oil and the like but magnesium stearate is preferred. A preferred amount is 0.2–3% by dry weight.

One or more binders, in an amount of 1–5% by weight may be chosen from binders generally available such as povidone (polyvinyl pyrrolidinone), starch paste or polymers but povidone is preferred.

A disintegrant, to aid in the breaking up and disintegration of the prepared formulation, is included in this formulation in an amount of 5–15% by dry weight. Any known disintegrant may be used herein but corn starch is preferred.

Choice of a diluent or diluents is at the discretion of the practitioner but, regular lactose is preferred. It is added in the percentage needed to bring the dry powder weight to unity.

The invention is further illustrated by the following examples of the preparation of tablet and pill forms of ticlopidine HCl. These examples are by no means intended to limit the scope of this invention but are given by way of illustration.

EXAMPLE I

| Ingredients | Tablets Grade | Grams Per 20,000 Tab |
|---|---|---|
| Ticlopidine hydrochloride | | 5,000 g |
| Lactose, regular | USP | 1.747 |
| Povidone (K29-32) | USP | 156 |
| Citric acid anhydrous | USP | 78 |
| Cornstarch | USP | 780 |
| Magnesium stearate | USP | 39 |
| Total wt. | | 7,800 g |
| Purified water | USP | 1,350 ml |

Tablets are prepared as follows: Ticlopidine hydrochloride and lactose are mixed in a planetary mixer for 10 minutes. Povidone and citric acid are dissolved in 1,350 ml of purified water and added slowly with continuous mixing to the drug/lactose mixture. The resultant wet granulation is mixed for 5 minutes and then passed through a number 4 or number 8 screen. The granulation is dried at 40° C. to between 0.5%–1.5% moisture content and passed through a number 16 screen. The magnesium stearate and corn starch are thoroughly mixed and the mixture is blended with the dried, screened granulation and mixed for 5 minutes. If the moisture content is between 1.5%–2.5%, the granulation is compressed into tablets. As a final step the tablets are given an appropriate coating.

If necessary, an organic solvent such as methanol, ethanol or the like can be substituted for water as the solvent in the above procedure.

EXAMPLE II

| Ingredient | Capsules Grade | Grams Per 10,000 Caps |
|---|---|---|
| Ticlopidine hydrochloride | | 2,500 g |
| Microcryst. cellulose (Avicel PH 101) | USP | 873.5 |
| Povidone (K29-32) | USP | 78.0 |
| Citric acid anhydrous | USP | 39.0 |
| Cornstarch | USP | 390.0 |
| Magnesium stearate | USP | 9.75 |
| Stearic acid (powder) | USP | 9.75 |
| Total wt. | | 3,900.0 g |

| | Capsules | |
|---|---|---|
| Ingredient | Grade | Grams Per 10,000 Caps |
| Purified water | USP | 700 ml |

Capsules are prepared as follows: Ticlopidine hydrochloride and lactose are mixed in a planetary mixer for 10 minutes. Povidone and citric acid are dissolved in 700 ml of purified water and slowly added with continuous mixing to the drug/lactose mixture. Mixing is continued for 5 minutes after addition of the povidone/citric acid solution. The wet granulation is then passed through a number 4 or number 8 screen following which it is dried at 40° C. to 0.5%–1.5% moisture content. This dried granulation is then passed through a number 20 screen. The magnesium stearate and corn starch are mixed and then blended with the dried granulation and mixed for 5 more minutes. The moisture content is then checked to make sure it falls between 1.5%–2.5% moisture, and then 390 milligrams per capsule are transferred into brown, No. 1 opaque gelatin capsules. Here again methanol or ethanol can be substituted for water in the above procedure.

Although specific embodiments of the present invention have been described hereinabove it will be evident that various changes in the way of practicing it may be made within the spirit and scope of said invention.

What is claimed is:

1. A stable pharmaceutical composition comprising a therapeutically effective amount of an active ingredient which is a pharmaceutically acceptable acid addition salt (PAAS) of a compound having the formula

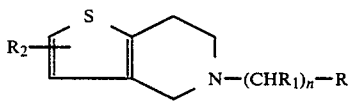

wherein:
R is phenyl or benzyl, each optionally substituted on the phenyl ring with 1 to 3 halogen atoms, alkyl of 1–6 carbon atoms, alkoxy of 1–6 carbon atoms, hydroxy or nitro;
$R_1$ is hydrogen, halogen, hydroxy or alkyl having 1–6 carbon atoms;
$R_2$ is hydrogen or halogen; and
n is 1 or 2, and when n is 2, $R_1$ may have different meaning in each ($CHR_1$) radical and a non-toxic stabilizing amount of a pharmaceutically acceptable non-volatile acidic compound which is cinnamic acid, glycolic acid, malonic acid, or mandelic acid; and at least one pharmaceutically acceptable excipient.

2. The composition of claim 1 wherein said acidic compound is present in an amount of 0.5–5.0% (w/w) relative to the active ingredient.

3. The composition of claim 2 wherein said compound is the hydrochloride salt of 5-(2-chlorobenzyl)-4,5,6,7-tetrahydrothieno[3,2-c]pyridine and said acid is present in an amount of 1–1.5% (w/w).

4. A pharmaceutical composition which comprises
40–90% by weight of a pharmaceutically acceptable acid addition salt of a thieno-pyridine derived compound;
0.5–5% by weight of a pharmaceutically acceptable, non-volatile organic acid which is cinnamic acid, glycolic acid, malonic acid, malic acid or mandelic acid;
0.2–5% by weight of a pharmaceutically acceptable lubricant;
5–15% by weight of a pharmaceutically acceptable disintegrant;
1–5% by weight of a pharmaceutically acceptable binder and the remainder a pharmaceutically acceptable diluent.

5. The composition of claim 4 wherein the compound is the hydrochloride salt of 5-(2-chlorobenzyl)-4,5,6,7-tetrahydrothieno[3,2-c]pyridine and said lubricant is magnesium stearate.

6. A process for preventing degradation of a pharmaceutically acceptable acid addition salt of a compound chosen from those represented by the formula

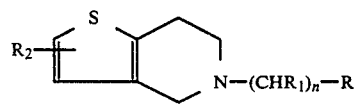

wherein:
R is phenyl or benzyl, each optionally substituted on the phenyl ring with 1 to 3 halogen atoms, alkyl of 1–6 carbon atoms, alkoxy of 1–6 carbon atoms, hydroxy or nitro;
$R_1$ is hydrogen, halogen, hydroxy or alkyl having 1–6 carbon atoms;
$R_2$ is hydrogen or halogen; and
n is 1 or 2, and when n is 2, $R_1$ may have different meaning in each ($CHR_1$) radical when formulated into dry compositions which process comprises adding a pharmaceutically acceptable non-volatile organic acid which is cinnamic acid, glycolic acid, malonic acid, malic acid, or mandelic acid to said composition during the formulation thereof.

7. The process of claim 6 wherein said acidic compound is present in an amount of 0.5–5.0% (w/w) relative to the active ingredient.

8. The process of claim 7 wherein said active ingredient is the hydrochloride salt of 5-(2-chlorobenzyl)-4,5,6,7-tetrahydrothieno[3,2-c]pyridine and said acid is present in an amount between 1–1.5% (w/w).

9. The process of claim 8 wherein there is a plurality of excipients which include a disintegrant, a lubricant, a binder and a diluent.

10. The process of claim 9 wherein the lubricant is magnesium stearate, the disintegrant is corn starch, the binder is povidone, and the diluent is lactose.

* * * * *